United States Patent
Brennan et al.

(10) Patent No.: US 9,417,255 B2
(45) Date of Patent: Aug. 16, 2016

(54) CAP CLOSURE WITH CANNULA

(71) Applicant: Siemens Healthcare Diagnostics Inc., Tarrytown, NY (US)

(72) Inventors: Joseph Brennan, Newark, DE (US); James Kegelman, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/769,429

(22) PCT Filed: Feb. 19, 2014

(86) PCT No.: PCT/US2014/017172
§ 371 (c)(1),
(2) Date: Aug. 20, 2015

(87) PCT Pub. No.: WO2014/130558
PCT Pub. Date: Aug. 28, 2014

(65) Prior Publication Data
US 2016/0003861 A1   Jan. 7, 2016

Related U.S. Application Data

(60) Provisional application No. 61/768,195, filed on Feb. 22, 2013.

(51) Int. Cl.
*B65D 51/22* (2006.01)
*G01N 35/00* (2006.01)
(Continued)

(52) U.S. Cl.
CPC ........ *G01N 35/1079* (2013.01); *B01L 3/50825* (2013.01); *B65D 51/22* (2013.01);
(Continued)

(58) Field of Classification Search
CPC .................... B01L 2200/0689; B01L 2300/04; B01L 2300/042; B01L 2400/0638; B01L 3/50; B01L 3/50825; B65D 51/20; B65D 51/22; B65D 47/36; B65D 47/38; G01N 2035/1025; G01N 35/0099; G01N 35/1002; G01N 35/1009; G01N 35/1011; G01N 35/1079
USPC ............. 436/43, 174, 180; 422/63, 68.1, 501, 422/509, 512, 517, 521, 547, 549, 550, 422/556; 435/287.3, 288.1; 215/247, 248, 215/249, 250, 253, 307, 354, 321, 329, 215/341; 220/260
See application file for complete search history.

(56) References Cited

U.S. PATENT DOCUMENTS 4,634,013 A * 1/1987 Bar-Kokhba ........ B65D 51/223
215/228
5,833,088 A    11/1998 Kladders et al.
(Continued)

FOREIGN PATENT DOCUMENTS

WO        2012/112486 A2    8/2012

OTHER PUBLICATIONS

PCT International Search Report and Written Opinion dated May 9, 2014 (11 Pages).

*Primary Examiner* — Maureen Wallenhorst
(74) *Attorney, Agent, or Firm* — Pepper Hamilton LLP

(57) ABSTRACT

An analyzer for use with in vitro diagnostics includes one or more containers. Each container includes a container body configured to hold one or more fluids, a closure device disposed on the container body and housing a movable cannula, and a sealing portion configured to seal off the one or more fluids in the container body from matter outside the container body when the sealing portion is closed. The system also includes one or more pick and place devices configured to move the one or more containers between different locations. The movable cannula is configured to move downward responsive to a force from the one or more pick and place devices and cause an opening in the sealing portion.

23 Claims, 12 Drawing Sheets

(51) Int. Cl.
*G01N 35/10* (2006.01)
*B01L 3/00* (2006.01)
*B65D 47/38* (2006.01)

(52) U.S. Cl.
CPC ........ *G01N35/0099* (2013.01); *G01N 35/1002* (2013.01); *G01N 35/1009* (2013.01); *G01N 35/1011* (2013.01); *B01L 2200/0689* (2013.01); *B01L 2300/042* (2013.01); *B01L 2400/0638* (2013.01); *B65D 47/38* (2013.01); *G01N 2035/1025* (2013.01)

(56) References Cited

U.S. PATENT DOCUMENTS

| | | | |
|---|---|---|---|
| 7,691,332 | B2 | 4/2010 | Kacian et al. |
| 2007/0034592 | A1 | 2/2007 | Pavlovic et al. |
| 2008/0251489 | A1 | 10/2008 | Livingston et al. |
| 2009/0035866 | A1* | 2/2009 | Wilson ............... G01N 35/0099 436/43 |
| 2015/0276774 | A1* | 10/2015 | Pollack .............. G01N 35/0902 414/749.1 |

* cited by examiner

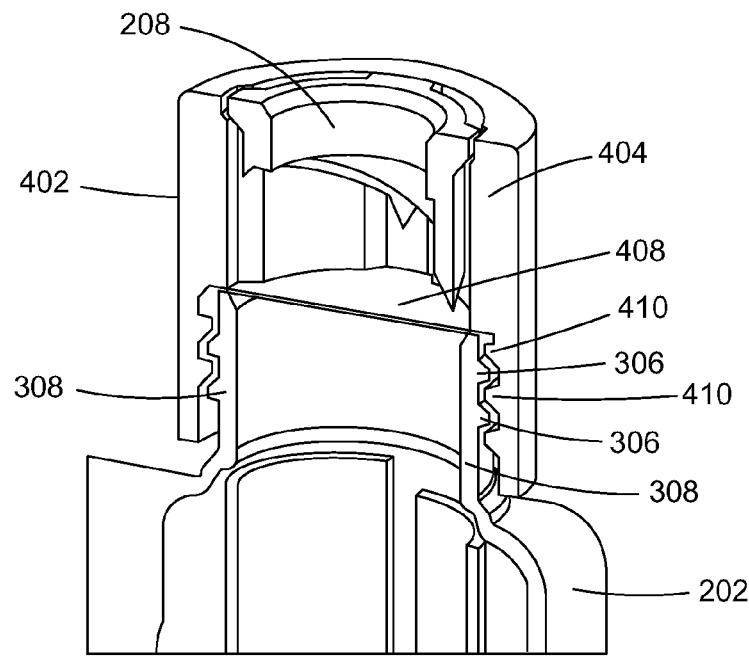
FIG. 4B
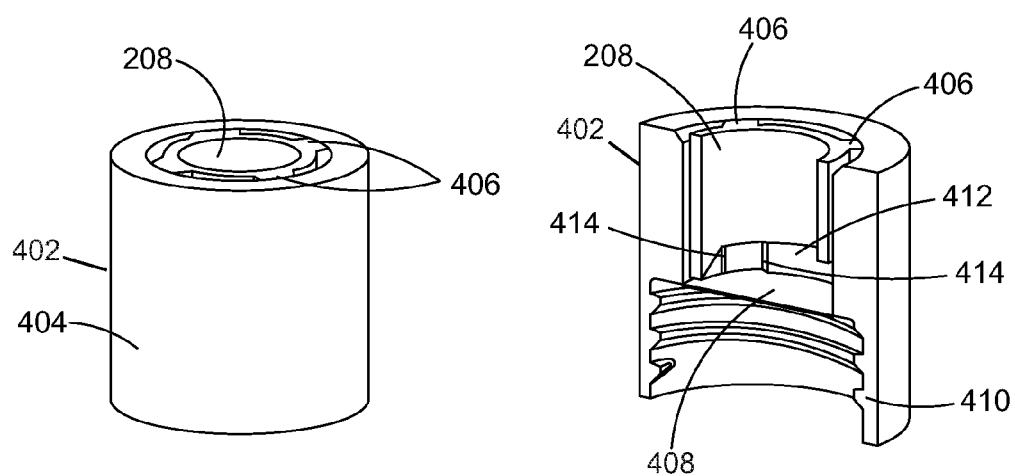
FIG. 4C
FIG. 4D

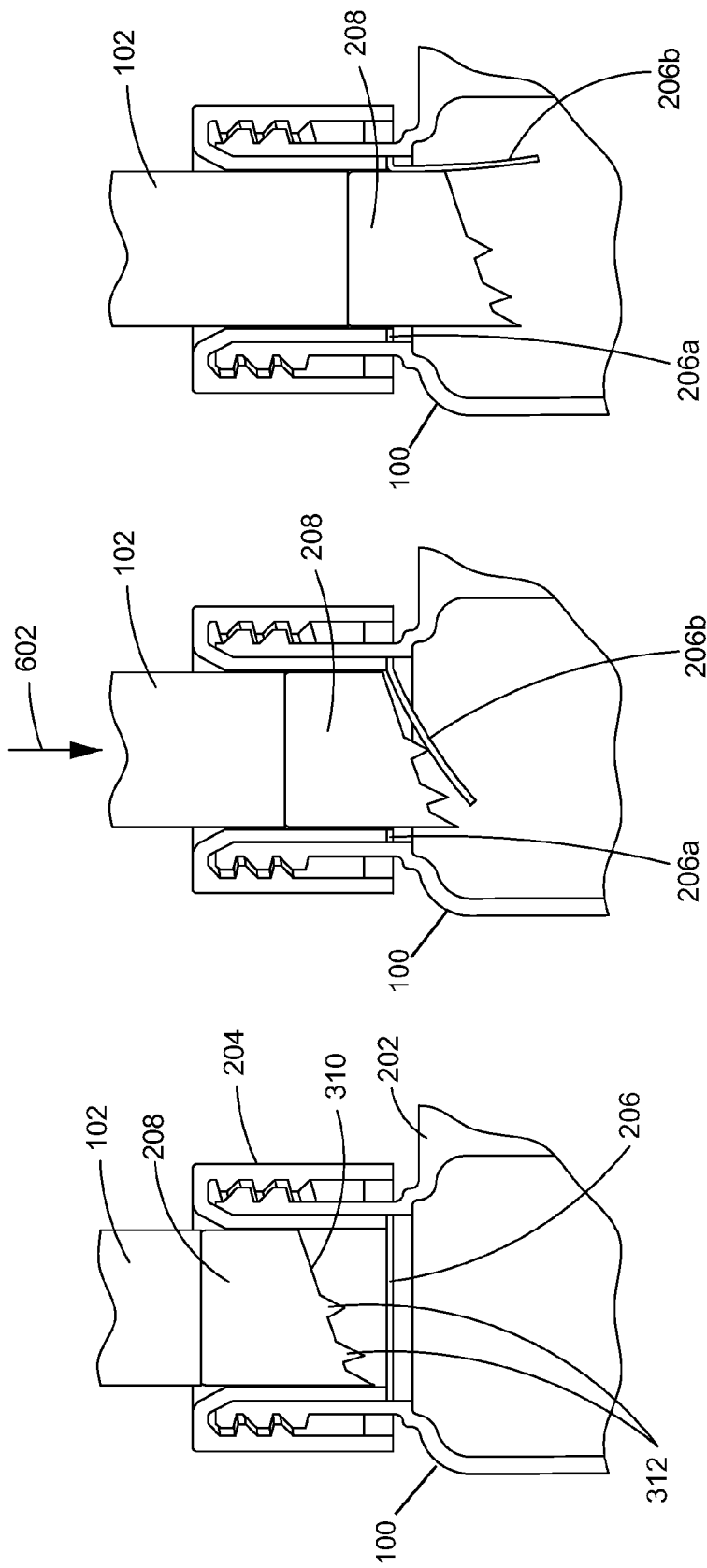

CAP CLOSURE WITH CANNULA

CROSS-REFERENCE TO RELATED APPLICATIONS

This application claims priority to U.S. provisional application Serial No. 61/768,195 filed Feb. 22, 2013, which is incorporated herein by reference in its entirety.

TECHNOLOGY FIELD

The present invention relates in general to systems and methods for opening containers and, more particularly, to systems and methods for opening sealing portions of containers using opening mechanisms housed in container closure devices.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples, have been loaded. The analyzer extracts a liquid sample from the vial and combines the sample with various reagent fluids (reagents) in special reaction cuvettes or tubes (referred to generally as reaction vessels).

Reagents to be combined with samples are contained in reagent containers, such as reagent wedges. In conventional systems, pick and place devices are used to hold reagent containers and transport the reagent containers between different locations of an analyzer. In some locations, reagent probes are used to aspirate reagents from their respective reagent containers and sense levels (e.g., capacitance level sensing) of reagents remaining in each of their respective reagent containers.

Reagent containers may include reagent container closure devices (e.g., caps) that seal the reagent containers and prevent evaporation of the reagents until they are opened for testing. Some conventional systems require manual opening (e.g., unscrewing cap) of the reagent container closure devices by human operators, thereby increasing operator workflow. Other conventional systems may include films to seal the reagents in the reagent containers. The films, which are punctured by the probes, may result in contamination of reagents along the length of the probes. The contaminated probes must then be cleaned, requiring significant cleaning time (e.g., 1-2 seconds per wash), thereby reducing throughput. Capacitance level sensing errors may also be caused by residual fluid and/or electric charge accumulation on the punctured film.

SUMMARY

Embodiments include an analyzer for use with in vitro diagnostics that has one or more containers. The one or more containers include a container body configured to hold one or more fluids, a closure device disposed on the container body and housing a movable cannula, and a sealing portion configured to seal off the one or more fluids in the container body from matter outside the container body when the sealing portion is closed. The analyzer also includes one or more pick and place devices configured to move the one or more containers between different locations. The movable cannula is configured to move downward responsive to a force from the one or more pick and place devices and cause an opening in the sealing portion.

According to an embodiment, the analyzer further includes a fluid contacting device configured to move downward through the opening in the sealing portion, contact the one or more fluids, and retract upward through the opening in the sealing portion. The movable cannula is further configured to cause the opening in the sealing portion to have a size sufficient to prevent the fluid contacting device from contacting the sealing portion.

According to one embodiment, the fluid contacting device is further configured to aspirate a portion of the one or more fluids in the container body. According to one embodiment, the fluid contacting device is further configured to sense the level of the one or more fluids in the container body.

In one embodiment, the analyzer further includes one or more sensors that sense position information indicating one or more positions of the one or more pick and place devices and a controller configured to control the one or more pick and place devices to move the cannula between a retracted position and an extended position based on the sensed position information.

In another embodiment, the one or more containers further comprises a container holding portion configured to be held by the one or more pick and place devices to move the one or more containers. The container holding portion has a recessed portion disposed on a top surface of the container body and a rib portion extending between opposing walls of the recessed portion.

According to an embodiment, the analyzer is connected to an automation system having a plurality of analyzers connected thereto.

Embodiments include a fluid container having a container body configured to hold one or more fluids and a closure device disposed on the container body and housing a movable cannula. The container also includes a sealing portion configured to seal off the one or more fluids in the container body from matter outside the container body when the sealing portion is closed. The movable cannula is configured to move in a downward direction responsive to a downward force and cause an opening in the sealing portion.

According to an embodiment, the sealing portion is attached to a bottom surface of the closure device. According to another embodiment, the sealing portion is housed in the closure device.

In one aspect of an embodiment, the sealing portion is a film membrane. In another aspect, the sealing portion is a molded membrane.

In one embodiment, the closure device is removably coupled to the container body. In one aspect of an embodiment, the closure device comprises threading and is rotatably coupled to the container body via the threading. In another aspect of an embodiment, the closure device is a snap cap.

In another embodiment, the closure device is fixed to the container body.

According to an embodiment, the fluid container further includes a retracted position holding mechanism that is configured to hold the cannula in a retracted position until the downward force is sufficient to overcome a resistance that holds the cannula in the retracted position.

According to an embodiment, the fluid container further includes an extended position holding mechanism that is configured to hold the cannula in an extended position.

Embodiments include a closure device for use with a container having a closure device body configured to be coupled to a container and a movable cannula housed in the closure device body and configured to move downward relative to the closure device body responsive to a downward force exerted on the cannula.

According to an embodiment, the closure device further includes a sealing portion housed in the closure device body, spaced below the cannula when the cannula is in an extended position and configured to be opened responsive to the downward force from the cannula exerted on the sealing portion.

According to another embodiment, the closure device further includes a coupling portion configured to couple the closure device body to a container.

In one embodiment, a bottom surface of the cannula is sloped toward a bottom of the closure device body. In other embodiment, a bottom surface of the cannula comprises one or more pointed edges.

Embodiments include a method for opening a container. The method includes applying a downward force to a cannula housed in a closure device of a fluid container and moving the cannula in a downward direction toward a sealing portion responsive to the downward force. The method also includes providing an opening in the sealing portion with the cannula by contacting the sealing portion with the cannula.

According to an embodiment, the method further includes moving a fluid contacting device through the opening in the sealing portion, contacting one or more fluids in the fluid container with the fluid contacting device, and retracting the fluid contacting device back through the opening in the sealing portion. The opening of the sealing portion further includes causing the opening in the sealing portion to have a size sufficient to prevent the fluid contacting device from contacting the sealing portion.

According to another embodiment, the method further includes using a pick and place device to move the fluid container between different locations and applying the downward force to the cannula further includes applying the downward force with the pick and place device.

In one embodiment, the contacting of the one or more fluids in the fluid container further includes at least one of: (i) aspirating the one or more fluids in the fluid container into the fluid contacting device, and (ii) sensing the level of the one or more fluids in the fluid container.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 4B is a close-up perspective cross-sectional view of the induction seal closure device coupled to the exemplary fluid container shown at FIG. 4A that can be used with the embodiments disclosed herein;

FIG. 4C is a perspective view of the induction seal closure device shown in FIG. 4A that can be used with the embodiments disclosed herein;

FIG. 4D is a close-up cross-sectional view of the induction seal closure device shown in FIG. 4A that can be used with the embodiments disclosed herein;

FIG. 6A is a cross-sectional view of a top portion of an exemplary fluid container illustrating a pick and place device adjacent a cannula in a retracted position and a closed sealing portion that can be used with the embodiments disclosed herein;

FIG. 6B is a cross-sectional view of the exemplary fluid container shown at FIG. 6A illustrating the cannula having moved from the retracted position to an intermediate position and contacting the sealing portion that can be used with the embodiments disclosed herein;

FIG. 6C is a cross-sectional view of the exemplary fluid container shown at FIG. 6A illustrating the cannula in an extended position and an opening in the sealing portion that can be used with the embodiments disclosed herein;

DETAILED DESCRIPTION OF ILLUSTRATIVE EMBODIMENTS

Figure 1:
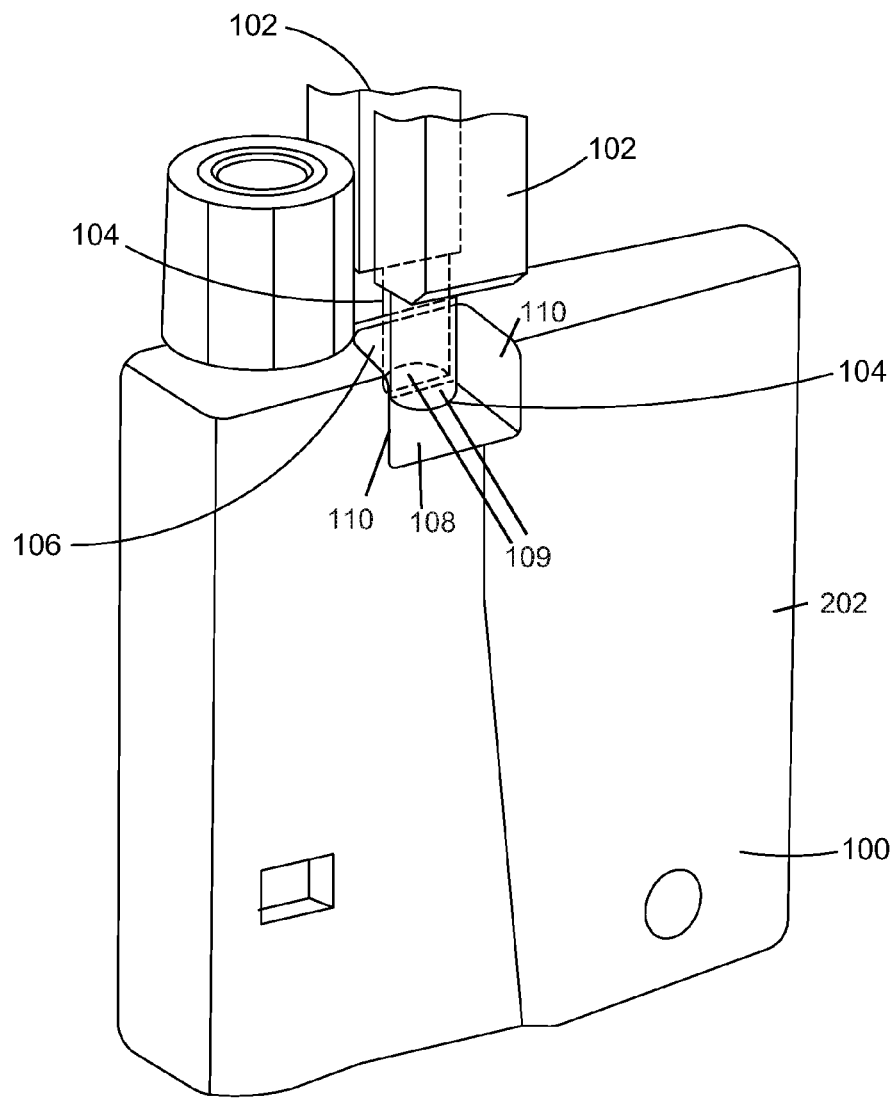
FIG. 1 is a perspective view of an exemplary fluid container held by a pick and place device that can be used with embodiments disclosed herein.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention include systems and methods that provide a more efficient analyzer for opening sealing portions (e.g., films and molded membranes) of containers (e.g., reagent containers). Embodiments of the present invention include container closure devices (e.g., caps) housing cannulas configured to open the sealing portions. Embodiments of the present invention avoid using reagent probes to open the sealing portions by utilizing pick and place devices to open the sealing portions, thereby eliminating contamination along the length of the probes and significantly reducing cleaning time of the probes. Embodiments of the present invention increase throughput by utilizing the pick and place devices to transport the containers and to cause the cannulas to open the sealing portions. Embodiments of the present invention improve operator workflow by utilizing the pick and place devices to automatically open the sealing portions via the cannulas housed in the container closure devices, thereby avoiding the need to manually open the sealing portions. Embodiments of the present invention increase throughput by providing openings in the sealing portions large enough to prevent contamination of probes that would otherwise require significant cleaning time.

Although the containers in the embodiments described herein are reagent containers holding various reagent fluids and used in an IVD analyzer and/or automation system, other embodiments may include containers holding other types of fluids (e.g., samples). Embodiments may also include containers used in other types of environments.

FIG. 1 is a perspective view of an exemplary reagent fluid container 100 held by a pick and place device 102. Automation systems, such as IVD automation systems, may include one or more analyzers. An analyzer may include one or more pick and place devices, such as pick and place device 102, which may be used to transport a plurality of reagent containers 100 between different locations of the analyzer. As shown in FIG. 1, pick and place device 102 may include a pair of holding mechanisms 104 having geometries configured to grip a rib portion 106. The geometry of the pick and place device 102 shown in the embodiment at FIG. 1 is merely exemplary. Other embodiments may include pick and place devices having different geometries that are configured to transport reagent containers between different locations and apply a force to the cannulas to cause the cannulas to open the sealing portion as described in more detail below with reference to the flow diagram of FIG. 9.

Figure 2:
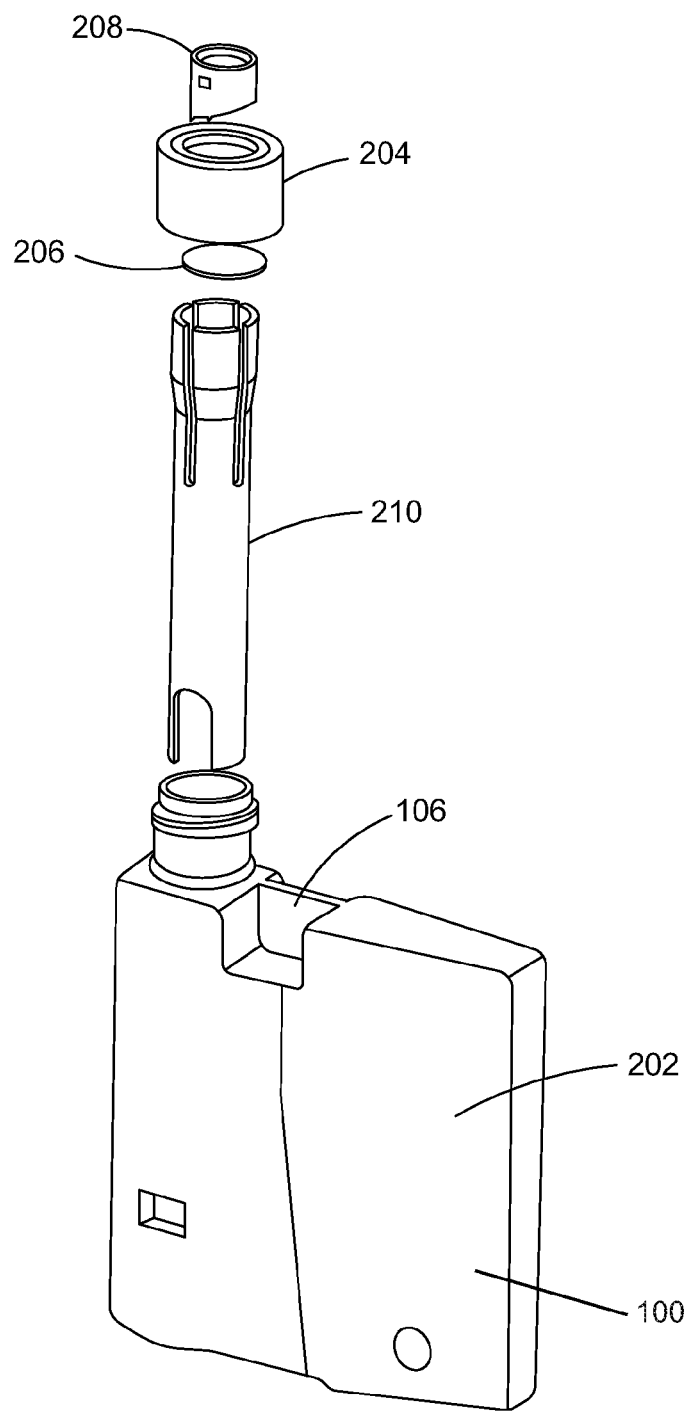
FIG. 2 is an exploded view of the exemplary fluid container shown at FIG. 1 that can be used with the embodiments disclosed herein.
Figure 3A:
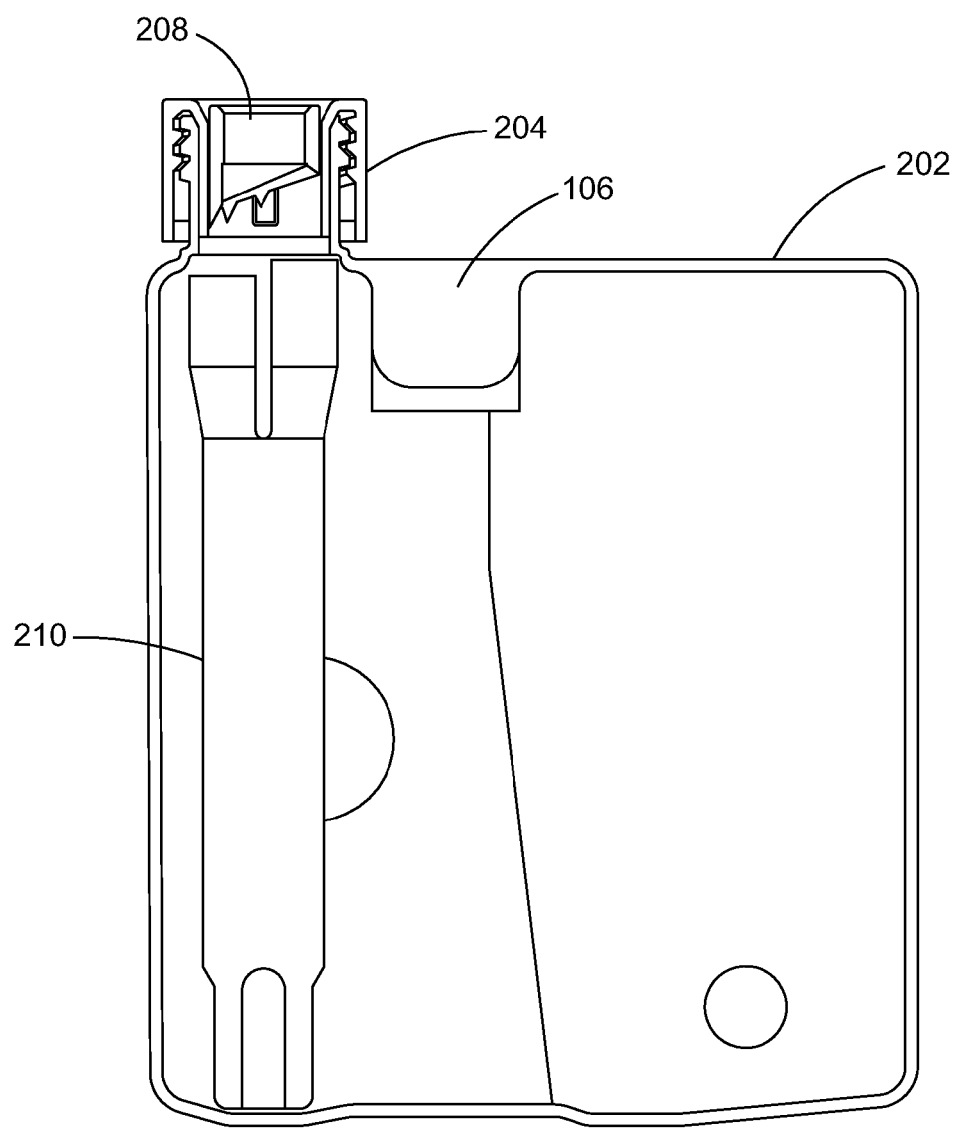
FIG. 3A is a cross-sectional view of the exemplary fluid container shown at FIG. 1 that can be used with the embodiments disclosed herein.
Figure 3B:
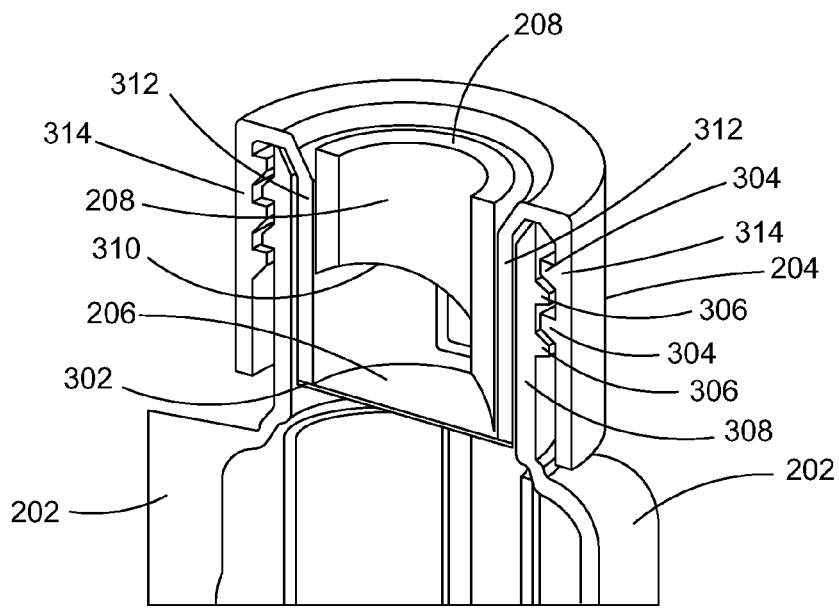
FIG. 3B is a close-up perspective cross-sectional view illustrating the conduction seal closure device of the exemplary fluid container shown at FIG. 1 that can be used with the embodiments disclosed herein.

FIG. 2 and FIG. 3A to FIG. 3D are various views and components of the exemplary reagent fluid container 100 shown at FIG. 1. The reagent fluid container 100 will now be described with reference to FIG. 2 and FIG. 3A to FIG. 3D. As shown at FIG. 2, reagent container 100 may include a container body 202, a closure device 204, a sealing portion 206, and an evaporation tube 210 (shown in FIGS. 2, 3A, and 7) configured to limit evaporation of one or more fluids (not shown) held in container body 202. As shown in FIG. 3A and FIG. 3B, closure device 204 may be disposed on the container body 202 and may house movable cannula 208 having a bottom surface 310.

As shown in the embodiment in FIG. 1, the pair of holding mechanisms 104 of pick and place device 102 may hold the container at rib portion 106. As shown, rib portion 106 may extend between opposing walls 110 of a recessed portion 108 disposed on a top of the container body 202. Placing the rib portion 106 at the top of the container body 202 provides a shorter travel distance for the pick and place device 102, which approaches the container 100 from above, thereby improving the accuracy of the pick and place device 102 and increasing throughput.

The geometry of the reagent container 100 shown in the embodiment in FIG. 1 is exemplary. Other embodiments may include reagent containers and other fluid containers having different geometries that are configured to hold one or more liquids. In some embodiments, fluid containers may have multiple wells to hold one or more liquids. In some aspects, each well may include its own closure device and a sealing portion.

Figures 3C, 3D:
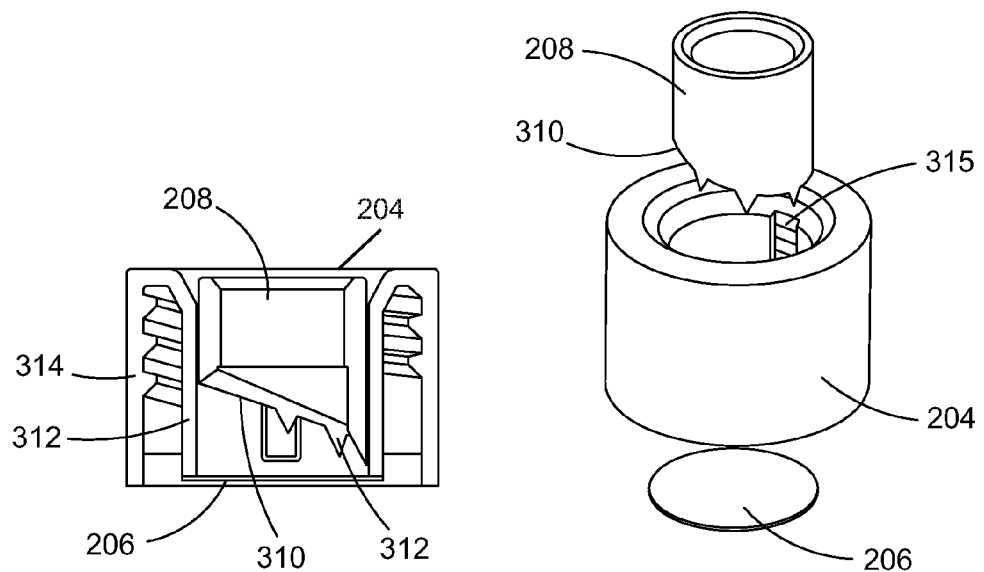
FIG. 3C is a cross-sectional side view of the conduction seal closure device of the exemplary fluid container shown at FIG. 1 that can be used with the embodiments disclosed herein.
FIG. 3D is a close-up exploded view of the conduction seal closure device of the exemplary fluid container shown at FIG. 1 that can be used with the embodiments disclosed herein.

In some embodiments, closure devices, such as closure device 204 may be a conduction seal cap. As shown in FIG. 3B and FIG. 3C, closure device 204 may include a conduction sealing film 206 configured to seal off the one or more fluids in the container body 202 from matter outside the container body 202 until the sealing film 206 is opened. For example, as shown in FIG. 3B, film 206 may be attached to a bottom surface 302 of inner portion 312 of the closure device 204 and configured to seal off matter outside the container body 202.

According to some embodiments, closure devices, such as closure device 204, may be removably coupled to the container body 202. For example, as shown in FIG. 3B, closure device 204 may be a rotatable cap that is rotatably removed from a container neck 308. As shown, the inner portion 312 of the conduction seal closure device 204 is disposed between the cannula 208 and container neck 308. Threads 304 are disposed on outer portion 314 and may engage threads 306 of container neck 308 to couple and remove closure device 204 from container body 202. In some aspects, fluid containers may include other types of removably coupled closure devices such as crimped crown caps, friction fit caps, snap caps, and the like. In some embodiments, fluid containers may include closure devices that are fixedly attached to container bodies.

In some embodiments, closure devices may be manufactured to include sealing portions. In other embodiments, removable closure devices may not include sealing portions. For example, some embodiments may include sealing portions, such as aluminum films and other sealing membranes (e.g., molded membranes), attached to surfaces of reagent container bodies.

The bottom surfaces of cannulas may be configured in different ways. For example, as shown in the embodiment in FIG. 3C, a bottom surface 310 of cannula 208 may be sloped toward sealing film 206. In some aspects, the bottom surface 310 of the cannula 208 may include one or more pointed edges, such as teeth 312, which may aid in the opening of sealing portions, such as sealing film 206, when they move downward and contact the sealing film 206, as described in more detail below with reference to the flow diagram of FIG.

9. The geometries of the closure device 204 and the cannula 208 shown in FIG. 2 and FIG. 3A to FIG. 3D are merely exemplary. Other embodiments may include closure devices and cannulas having different geometries configured to open sealing portions when they move downward and contact the sealing portions. In some embodiments, bottom surfaces of cannulas may extend from an outer perimeter toward a center axis as they slope toward sealing portions, thereby having pointed edges at centers of their bottom surfaces to aid in the opening of sealing portions.

Closure devices, such as closure device 204, may also include holding mechanisms, such as detent 315, configured to hold cannula 208 in a plurality of desired positions, such as retracted positions and extended positions. For example, detent 315 may be configured to hold the cannula 208 in a retracted position until a downward force upon the cannula 208 is sufficient to overcome a resistance that holds the cannula 208 in the retracted position shown in FIG. 6A. Detent 315 may be also be configured to hold the cannula 208 in the extended position shown in FIG. 6B after the cannula 208 has moved opened the sealing film 206. Other embodiments may include other types of holding mechanisms, such as breakaway web couplers 406, shown in FIG. 4D, notches, pins, levers, and the like.

Figure 4A:
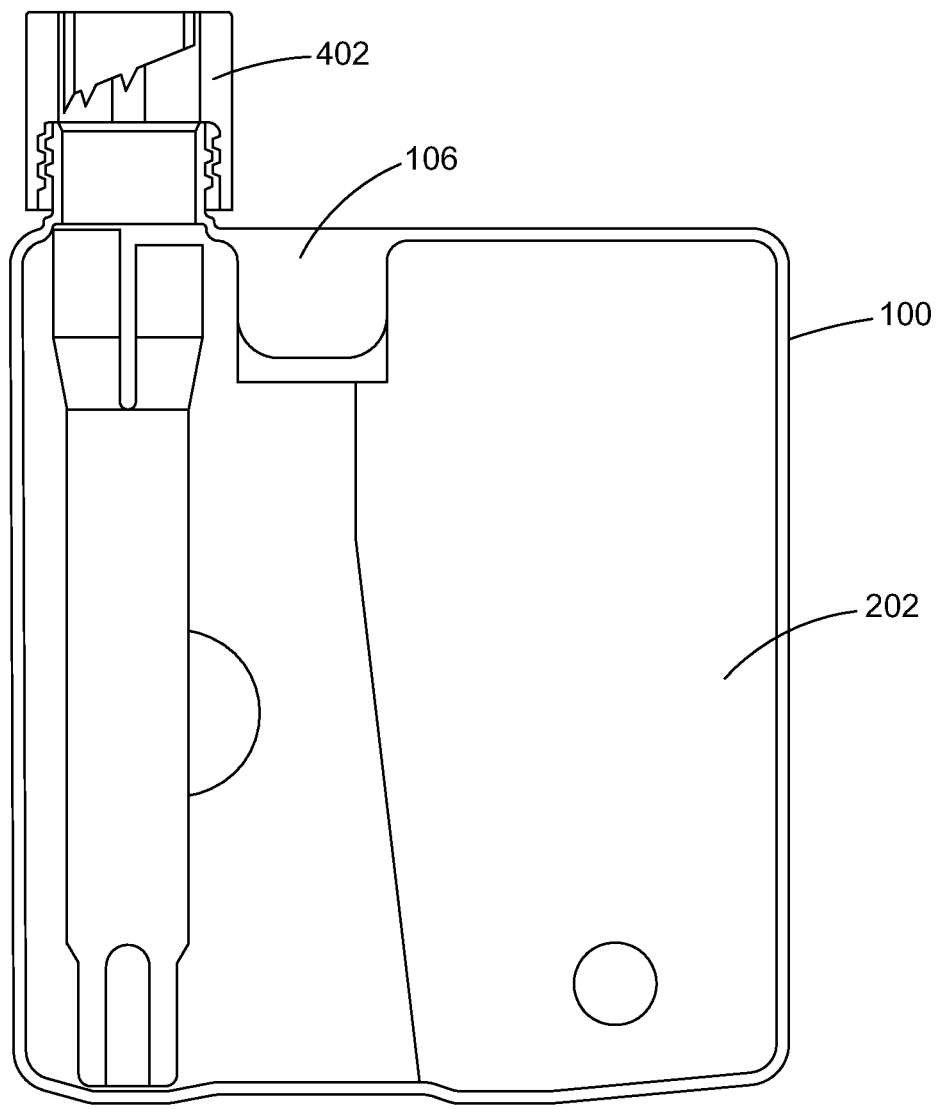
FIG. 4A is a cross-sectional view of an exemplary fluid container having an induction seal closure device that can be used with the embodiments disclosed herein.

In some embodiments, as shown in FIGS. 4A to FIG. 4E, fluid containers may include induction sealed closure devices, such as induction sealed closure device 402. As shown in FIG. 4B, the induction sealed closure device 402 may include a housing 404 that houses the induction sealing film 408. As shown in FIG. 4B, the housing 404 may include threads 410 disposed on inner surface of housing 404 that may engage threads 306 of container neck 308 to couple and remove closure device 402 from container body 202.

Figure 4E:
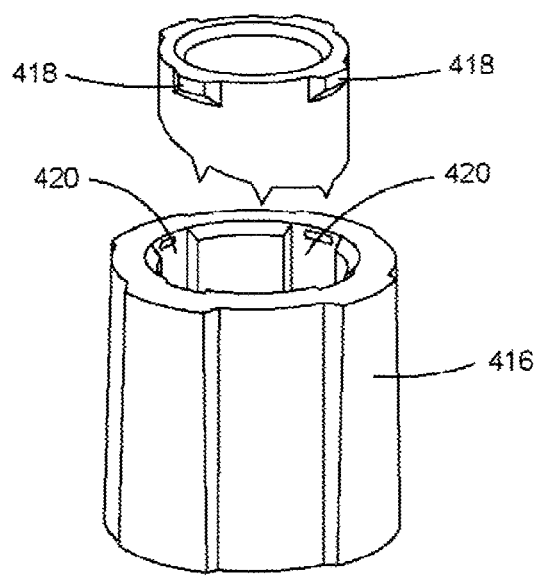
FIG. 4E is a close-up exploded view of the induction seal closure device shown in FIG. 4A that can be used with the embodiments disclosed herein.

As shown in FIG. 4C, induction sealed closure device 402, cannula 208, and breakaway web couplers 406 may be molded together as a single induction sealed closure device 402. The cannula 208 may also be slidably coupled to an inner surface 412 (shown in FIG. 4D) of the closure device 402. For example, as shown in FIG. 4D, closure device 402 may include grooves 414 that may be configured to guide the cannula 208 as it slides downward toward induction sealing film 408. The number and shape of the grooves 414 shown in FIG. 4D is exemplary. Aspects may include grooves having any number and shape. In another aspect, as shown in FIG. 4E, the induction seal closure device 416 includes protrusions 418 that may engage wide grooves 420.

Figure 5A:
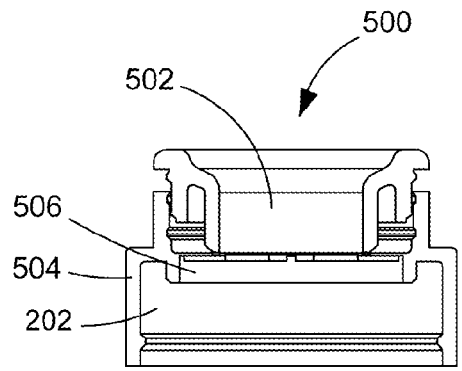
FIG. 5A is a cross-sectional side view of an exemplary molded closure device having a bottom surface of a cannula parallel to a molded membrane that can be used with the embodiments disclosed herein.
Figure 5B:
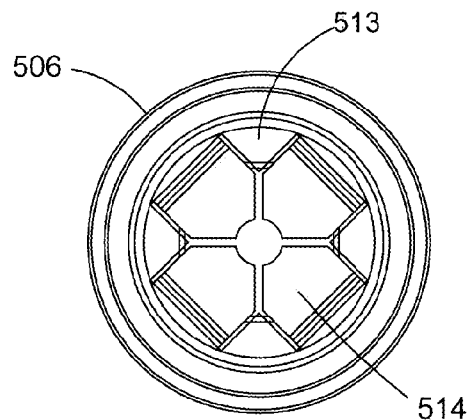
FIG. 5B is a bottom view of the exemplary molded membrane shown in FIG. 5A that can be used with the embodiments disclosed herein.
Figure 5C:
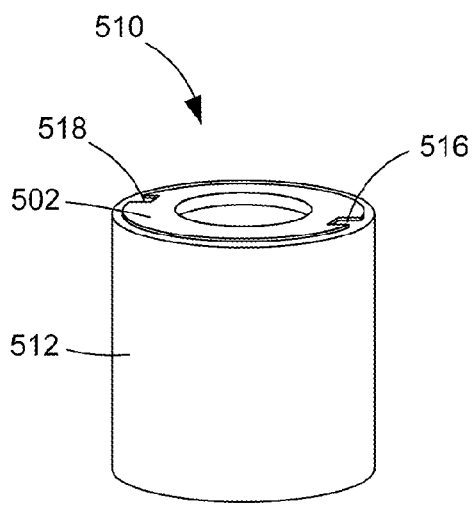
FIG. 5C is a perspective view of an exemplary molded closure device that can be used with the embodiments disclosed herein.
Figure 5D:
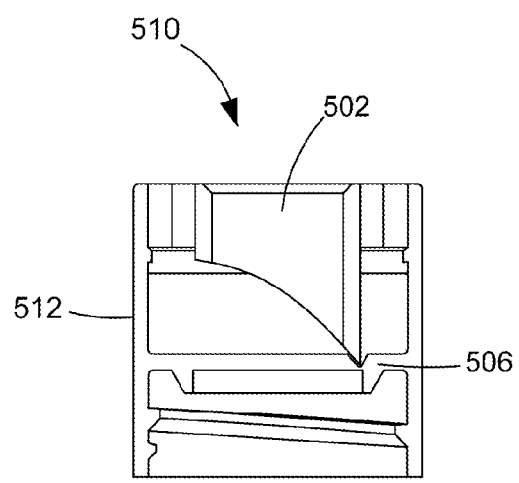
FIG. 5D is a cross-sectional side view of the exemplary molded closure device shown in FIG. 5C illustrating a bottom surface of a cannula sloped toward a molded membrane that can be used with the embodiments disclosed herein.

In some embodiments, closure device may include separately molded components. For example, as shown in FIG. 5A, closure device 500 includes cannula 502 that is molded separately from housing 504 of closure device 500. Containers may also include molded sealing portions. For example, as shown in FIG. 5A, a molded sealing membrane 506 may be molded on the container body 202. In some embodiments, a closure device 510 may include the molded sealing membrane 508. For example, as shown in FIG. 5D, the housing 512 and the molded sealing membrane 508 are molded together. As shown in FIG. 5B, a bottom surface 513 of molded membrane 506 may include a pattern 514 configured to cause portions of the molded membrane 506 to open to desired positions when the molded membrane 506 is opened by the cannula 502. As shown in FIG. 5C, housing 512 of sealed closure device 510 may be molded separately from cannula 502. As further shown in FIG. 5C, embodiments may include a housing 512 having protrusions 516 configured to engage grooves 518 of cannula 502. The protrusions 516 and grooves 518 may be used to guide the cannula 502 as the cannula 502 moves downward to a position where the cannula 502 contacts the molded membrane 506 shown in FIG. 5D.

In some embodiments, the geometries of pick and place devices, such as pick and place device 102 shown in FIG. 1, may be configured to: (i) transport containers 100 to different locations and (ii) apply forces to cannulas, such as cannula 208, to open sealing portions, such as sealing film 206. For example, as described above with regard to FIG. 1, pick and place device 102 may include a pair of separate holding mechanisms 104 to grip the rib portion 106. These separate holding mechanisms 104, each having semi-circular shaped bottom surfaces 109 may also be positioned together to have a single circular bottom surface that is shaped substantially the same as the top surface of cannula 208. A force may then be applied by the pick and place device 102 to the cannula 208 when the pick and place device 102 engages the top surface of the cannula 208, causing cannula 208 to move downward and open sealing film 206. Accordingly, the automated pick and place device 102 may be utilized as both a transport device and a device used to open sealing portions of containers, thereby improving workflow and increasing throughput.

FIG. 6A is a cross-sectional view of a top portion of an exemplary fluid container 100 illustrating cannula 208 in a retracted position. As shown, pick and place device 102 is in a position abutting cannula 208 prior to exerting a downward force on cannula 208. As described above with regard to FIG. 3D, holding mechanisms, such as detent 315 (shown in FIG. 3D), may be configured to hold the cannula 208 in the retracted position until a downward force upon the cannula 208 is sufficient to overcome a resistance that holds the cannula 208 in the retracted position shown in FIG. 6A.

FIG. 6B shows cannula 208 in an intermediate position having moved from the retracted position shown in FIG. 6A, responsive to a downward force from pick and place device 102, in the direction indicated by arrow 602. As shown in FIG. 6B, cannula 208 contacts sealing film 206 (shown in FIG. 6A), separating film portion 206a from film portion 206b, causing an opening in film 206.

As shown in FIG. 6C, cannula 208 is in an extended position that causes separated film portion 206b to move to the side and further from film portion 206a. As described above, holding mechanisms, such as detent 315 (shown in FIG. 3D), may be configured to hold the cannula 208 in the extended position shown in FIG. 6B after the cannula 208 has opened the sealing film 206. The locations of the cannula 208 and film portions 206a and 206b shown in FIG. 6B and FIG. 6C are exemplary. Embodiments may include other types of cannulas, such as cannula 502 in FIG. 5A, and other types of sealing portions, such as molded membrane 506 in FIGS. 5A and 5B, where the sealing portions may open in different directions at different locations relative to the cannulas. Embodiments may include one or more portions of sealing devices separated from and/or moved to positions different from the position of film portion 206a.

Figure 7:
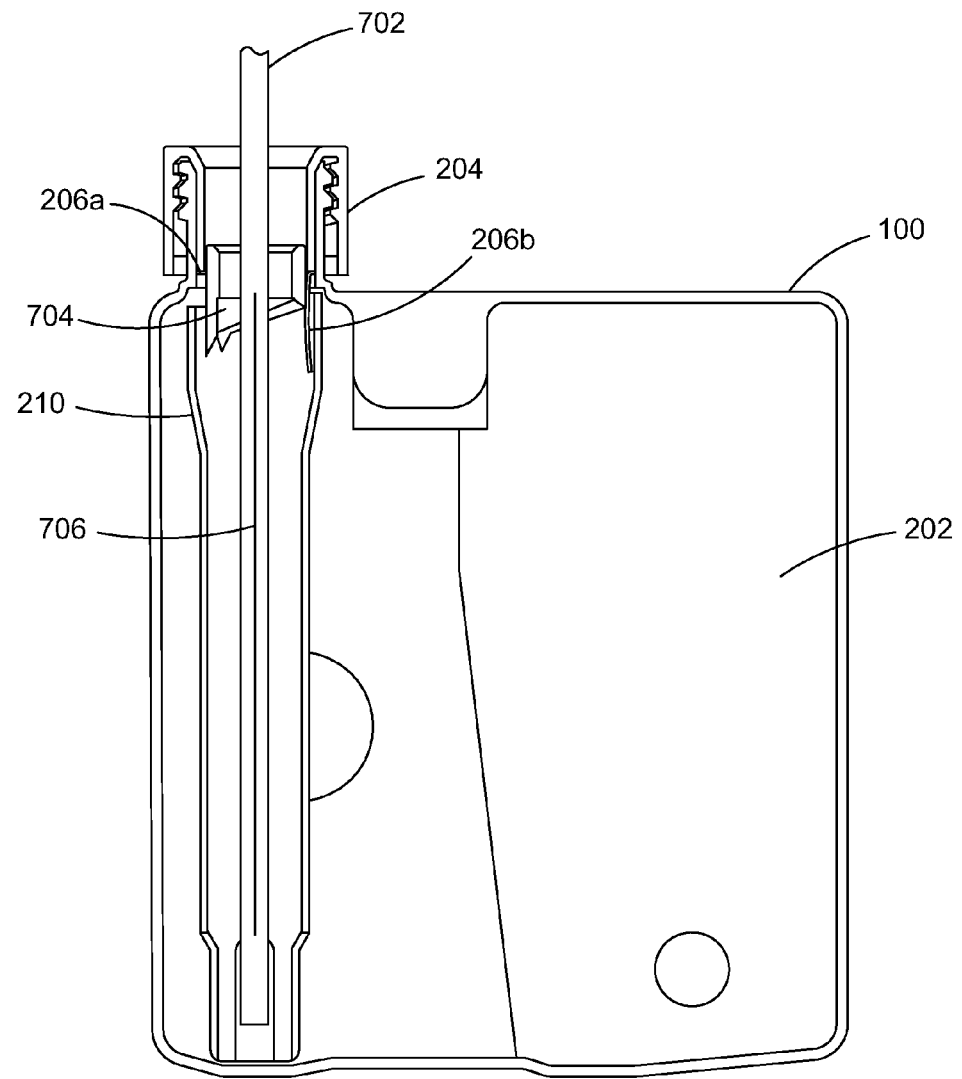
FIG. 7 is a cross-sectional view of an exemplary fluid container and a fluid contacting device that can be used with the embodiments disclosed herein.

FIG. 7 is a cross-sectional view of an exemplary fluid container 100 and a fluid contacting device 702 positioned within container body 202. As shown in FIG. 7, fluid contacting device 702 may be a probe that is used to aspirate one or more fluids from container 100. Probe 702 may also include capacitive level sensors 706 to sense levels of the one or more liquids remaining within the container body 202. Probe 702 is positioned through opening 704 between film portion 206a and separated film portion 206b, providing a space between the perimeter of probe 702 and film portion 206a and a space between the perimeter of probe 702 and separated film portion 206b sufficient to prevent the probe 702 from contacting film portion 206a and separated film portion 206b, thereby preventing contamination of probe 702. Preventing probe 702 from contamination of liquid residue on sealing film 206 reduces cleaning time from the time needed to clean the length of the probe 702.

Figure 8:
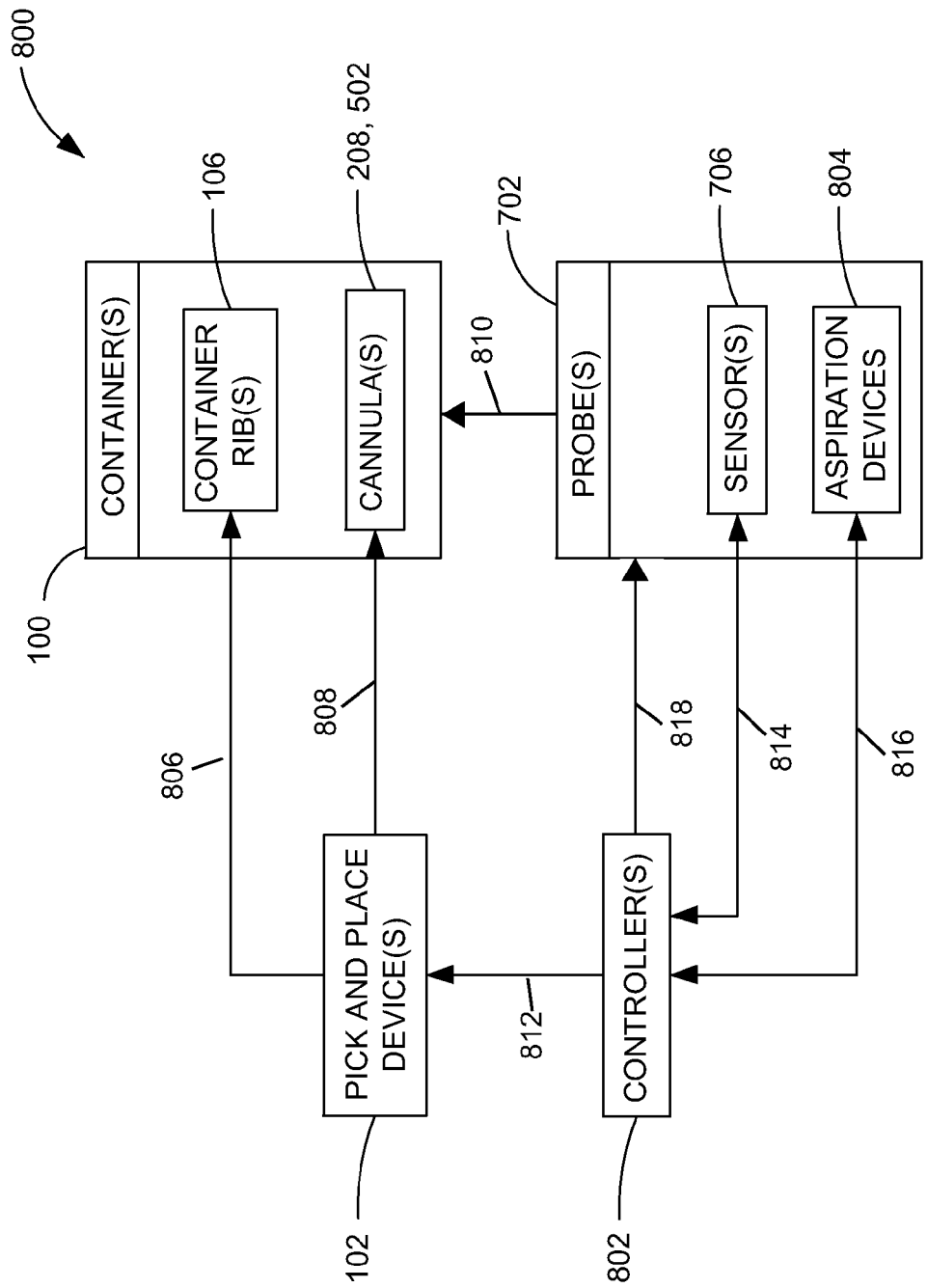
FIG. 8 is a block diagram of an exemplary analyzer for use with in vitro diagnostics that can be used with the embodiments disclosed herein.

FIG. 8 is a block diagram of an exemplary analyzer. As shown in FIG. 8, the analyzer 800 may include one or more reagent containers 100, one or more pick and place devices 102, one or more probes 702, and one or more controllers 802. The one or more containers 100 may each include container rib 106 and a cannula, such as cannula 208 or cannula 502. The one or more probes may each include a sensor, such as a capacitive level sensor 706 configured to sense the level of fluid remaining in their corresponding container 100, and aspiration devices 804, such as suction pumps, motors, actuators, etc., configured to aspirate one or more liquids from the one or more containers 100 into the corresponding probe 702.

Arrows 806, 808, and 810 in FIG. 8 indicate physical interaction between components of the system. For example, the one or more pick and place devices 102 may be configured to: (i) transport the one or more reagent containers 100 to different locations by gripping container ribs 106, indicated by arrow 806, and (ii) apply forces to cannulas 208, 502, indicated by arrow 808, to open sealing portions. The probes may be configured to be positioned within the one or more containers 100, as indicated by arrow 810, and moved between different locations.

Arrows 812, 814, 816, and 818 in FIG. 8 indicate communication (e.g., electronic communication, optical communication) between the one or more controllers 802 and components of the system. For example, controller 802 may include a main controller and one or more sub-controllers, each configured to communicate with the one or more pick and place devices 102, as indicated by arrow 812, to cause the one or more pick and place devices 102 to: (i) transport the one or more reagent containers 100 to different locations by gripping container ribs 106, and (ii) apply forces to cannulas 208, 502 to open sealing portions 206, 408, 506, and 508. Controller 802 may also be configured to communicate with the one or more probes 702, as indicated by arrow 818, to cause the one or more probes 702 to move between different locations and instruct the probe to be positioned within the one or more containers 100 for aspiration and/or level sensing. Controller 802 may also be configured to communicate with capacitive level sensors 706, as indicated by arrow 814, to receive sensed information from the capacitive level sensors 706 and cause capacitive level sensors 706 to perform operations (e.g., turn on, turn off). Controller 802 may also communicate with control aspiration devices 804, as indicated by arrow 816, to cause aspiration devices 804 to aspirate one or more liquids from the one or more containers 100 and receive status information from the aspiration devices 804.

Figure 9:
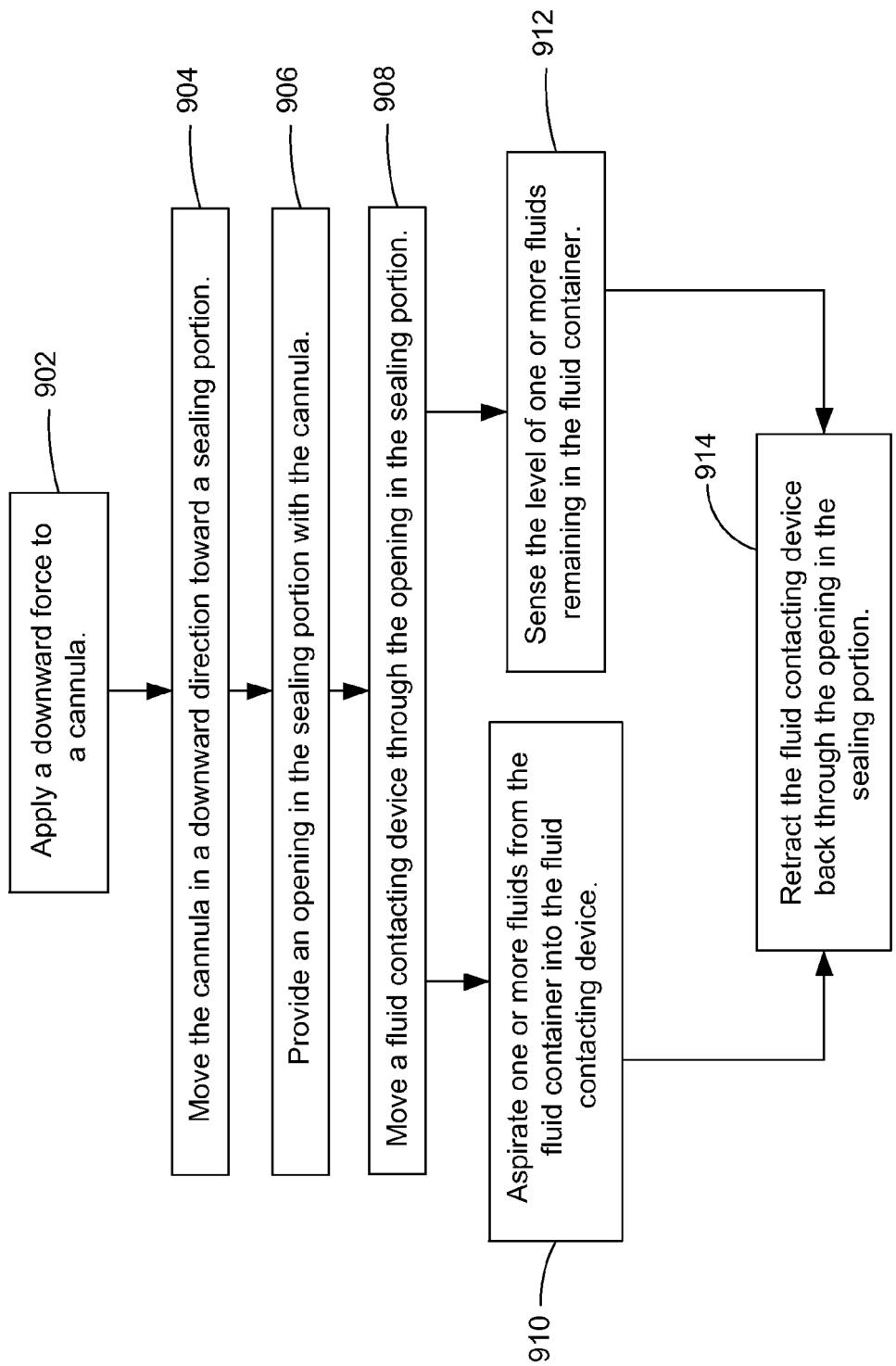
FIG. 9 is a flow diagram illustrating a method for accessing a container that can be used with the embodiments disclosed herein.

FIG. 9 is a flow diagram illustrating a method for accessing a container, such as container 100. For simplification purposes, the method will be described with reference to the components shown in FIGS. 6A, 6B, 7, and 8. The method described below may, however, be performed using components other than those shown in FIGS. 6A, 6B, 7, and 8. As shown at block 902 in FIG. 9, the method may include applying a downward force to a cannula, such as cannula 208, which is housed in closure device 204 of fluid container 100. The method may be embodied in automation systems, such as IVD automation systems, and analyzers, such as IVD analyzers. For example, while the cannula 208 is in the retracted position shown in FIG. 6A, the force may be applied by an automated pick and place device 102 to the cannula 208. As described above, because the pick and place device 102 may also be used to move containers 100 between different locations, the pick and place device 102 may be used to perform multiple tasks, thus improving operator workflow while increasing throughput.

As shown at block 904 in FIG. 9, the method may include moving the cannula 208 in the downward direction 602 toward a sealing portion, such as sealing portion 206. For example, the cannula 208 may be configured to move downward in the direction indicated by arrow 602, responsive to the force from a pick and place device 102. During its downward movement, the cannula 208 may move to the intermediate position shown at FIG. 6B.

As shown at block 906 of FIG. 9, an opening may be provided in the sealing portion 206 with the cannula 208 by contacting the sealing portion 206 with the cannula 208. For example, the film 206 may be opened when a bottom surface 310 (shown in FIG. 6A) and pointed edges, such as teeth 312, contact film 206, causing an opening in film 206 by separating film 206 into portion 206a and 206b.

After the opening is provided in the sealing portion 206, a fluid contacting device, such as probe 702 (shown in FIG. 7), may be moved through the opening 704 in the sealing portion 206, as shown at block 908 in FIG. 9. As shown in FIG. 7, the opening 704 of the sealing portion includes a size sufficient to prevent the fluid contacting device 702 from contacting the sealing portion 206a and sealing portion 206b.

In some embodiments, the probe may perform one or more tasks within the container. For example, as shown at block 910, the probe may aspirate one or more fluids in the fluid container 100 into the probe 702. The probe 702 may also sense the level of the one or more fluids in the fluid container 100 using the sensors 706, as shown at block 912.

The probe 702 may then be retracted back through the opening 704 in the sealing portion 206 without depositing any fluids on the sealing portion 206 or contacting any fluids or other objects that may be disposed on the sealing portion 206, preventing contamination of the probe 702 and reducing probe cleaning time.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An analyzer for use with in vitro diagnostics comprising:
one or more containers comprising:
a container body configured to hold one or more fluids;
a closure device disposed on the container body and housing a movable cannula; and
a sealing portion attached to one of the container body or the closure device, and configured to seal off the one or more fluids in the container body from matter outside the container body when the sealing portion is closed; and
one or more pick and place devices configured to move the one or more containers between different locations;
wherein the movable cannula is configured to move downward responsive to a force from the one or more pick and place devices and cause an opening in the sealing portion.

2. The analyzer of claim 1, further comprising a fluid contacting device configured to move downward through the opening in the sealing portion, contact the one or more fluids and retract upward through the opening in the sealing portion, wherein the movable cannula is further configured to cause the opening in the sealing portion to have a size sufficient to prevent the fluid contacting device from contacting the sealing portion.

3. The analyzer of claim 2, wherein the fluid contacting device is further configured to aspirate a portion of the one or more fluids in the container body.

4. The analyzer of claim 2, wherein the fluid contacting device is further configured to sense a level of the one or more fluids in the container body.

5. The analyzer of claim 1, further comprising:
one or more sensors that sense position information indicating one or more positions of the one or more pick and place devices; and
a controller configured to control the one or more pick and place devices to move the cannula between a retracted position and an extended position based on the sensed position information.

6. The analyzer of claim 1, wherein the one or more containers further comprises a container holding portion configured to be held by the one or more pick and place devices to move the one or more containers, the container holding portion having a recessed portion disposed on a top surface of the container body and a rib portion extending between opposing walls of the recessed portion.

7. The analyzer of claim 1, wherein the analyzer is part of automation system having a plurality of analyzers.

8. A fluid container comprising:
a container body configured to hold one or more fluids;
a closure device disposed on the container body and housing a movable cannula;
a sealing portion attached to one of the container body or the closure device, and configured to seal off the one or more fluids in the container body from matter outside the container body when the sealing portion is closed;
a retracted position holding mechanisms configured to hold the cannula in a retracted position; and
an extended position holding mechanism configured to hold the cannula in an extended position;
wherein the movable cannula is configured to move in a downward direction responsive to a downward force and cause an opening in the sealing portion, when the downward force is sufficient to overcome a resistance that holds the cannula in the retracted position in which the cannula does not open the sealing portion, the downward force moving the cannula to the extended position when the cannula opens the sealing portion.

9. The fluid container of claim 8, wherein the sealing portion is attached to a bottom surface of the closure device.

10. The fluid container of claim 8, wherein the sealing portion is housed in the closure device.

11. The fluid container of claim 8, wherein the sealing portion is a film membrane.

12. The fluid container of claim 8, wherein the sealing portion is a molded membrane.

13. The fluid container of claim 8, wherein the closure device is removably coupled to the container body.

14. The fluid container of claim 13, wherein the closure device comprises threading and is rotatably coupled to the container body via the threading.

15. The fluid container of claim 13, wherein the closure device is a snap cap.

16. The fluid container of claim 8, wherein the closure device is fixed to the container body.

17. A closure device for use with a container comprising:
a closure device body configured to be coupled to the container;
a movable cannula housed in the closure device body and configured to move downward relative to the closure device body from a retracted position to an extended position, responsive to a downward force exerted on the cannula;
a sealing portion housed in the closure device body and configured to seal off the container when the sealing portion is closed;
wherein the downward force exerted on the cannula causes an opening in the sealing portion, when the downward force is sufficient to overcome a resistance that holds the cannula in the retracted position in which the cannula does not open the sealing portion, the downward force moving the cannula to the extended position when the cannula opens the sealing portion.

18. The closure device of claim 17, further comprising a coupling portion configured to couple the closure device body to the container.

19. The closure device of claim 17, wherein a bottom surface of the cannula is sloped toward a bottom of the closure device body.

20. The closure device of claim 17, wherein a bottom surface of the cannula comprises one or more pointed edges.

21. A method for opening a container, comprising:
using a pick and place device to move a fluid container between different locations;
applying a downward force with the pick and place device to a cannula housed in a closure device disposed on the fluid container;
moving the cannula in a downward direction, response to the downward force, toward a sealing portion attached to one of the fluid container or the closure device; and
providing an opening in the sealing portion with the cannula by contacting the sealing portion with the cannula.

22. The method of claim 21, further comprising:
moving a fluid contacting device through the opening in the sealing portion;
contacting one or more fluids in the fluid container with the fluid contacting device; and
retracting the fluid contacting device back through the opening in the sealing portion,
wherein the opening of the sealing portion further comprises causing the opening in the sealing portion to have a size sufficient to prevent the fluid contacting device from contacting the sealing portion.

23. The method of claim 22, wherein the contacting of the one or more fluids in the fluid container further comprises at least one of: (i) aspirating the one or more fluids in the fluid container into the fluid contacting device, and (ii) sensing a level of the one or more fluids in the fluid container.

* * * * *